United States Patent
Elsesser et al.

(10) Patent No.: US 8,777,873 B2
(45) Date of Patent: Jul. 15, 2014

(54) WIRE GUIDE HAVING A RIB FOR COIL ATTACHMENT

(75) Inventors: James C. Elsesser, Bloomington, IN (US); Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 734 days.

(21) Appl. No.: 12/480,990

(22) Filed: Jun. 9, 2009

(65) Prior Publication Data
US 2009/0312670 A1 Dec. 17, 2009

Related U.S. Application Data
(60) Provisional application No. 61/061,196, filed on Jun. 13, 2008.

(51) Int. Cl.
*A61B 5/00* (2006.01)
*A61M 25/00* (2006.01)
*A61M 25/09* (2006.01)

(52) U.S. Cl.
CPC ..... *A61M 25/09* (2013.01); *A61M 2025/09083* (2013.01); *A61M 2025/09175* (2013.01)
USPC ........................................................ 600/585

(58) Field of Classification Search
USPC ................................. 600/585, 434
See application file for complete search history.

(56) References Cited

U.S. PATENT DOCUMENTS

| | | | |
|---|---|---|---|
| 4,796,642 A | 1/1989 | Harris | |
| 5,259,393 A | 11/1993 | Corso, Jr. et al. | |
| 5,282,478 A * | 2/1994 | Fleischhaker et al. | 600/585 |
| 5,365,945 A | 11/1994 | Jansen | |
| 5,415,170 A | 5/1995 | Hammerslag et al. | |
| 5,514,128 A | 5/1996 | Hillsman et al. | |
| 5,549,580 A | 8/1996 | Diaz | |
| 5,551,444 A * | 9/1996 | Finlayson | 600/585 |
| 5,666,969 A | 9/1997 | Urick et al. | |
| 5,724,989 A | 3/1998 | Dobson | |
| 5,833,705 A | 11/1998 | Ken et al. | |
| 6,322,572 B1 | 11/2001 | Lee | |
| 6,500,185 B1 | 12/2002 | Mathews et al. | |
| 2003/0225418 A1 | 12/2003 | Esksuri et al. | |
| 2005/0038359 A1* | 2/2005 | Aimi et al. | 600/585 |

OTHER PUBLICATIONS

Glebar—CAM.2 Profile Grinder—Product Summary—2 pages.

* cited by examiner

*Primary Examiner* — Brian Szmal
(74) *Attorney, Agent, or Firm* — Brinks Gilson & Lione

(57) ABSTRACT

The present invention generally relates to a medical surgical device and specifically a wire guide for percutaneous placement within a body cavity. In one embodiment, the wire guide includes an elongated core member having a proximal stop and a distal stop and a rib positioned between the proximal stop and the distal stop. A first coil is positioned over the elongated core member and extends between the proximal stop and the rib. A second coil is positioned over the elongated core member and extends between the rib and the distal stop.

15 Claims, 3 Drawing Sheets

WIRE GUIDE HAVING A RIB FOR COIL ATTACHMENT

RELATED APPLICATIONS

This non-provisional patent application claims priority to U.S. Provisional Patent Application No. 61/061,196, filed Jun. 13, 2008, the contents of which are incorporated by reference in their entirety.

TECHNICAL FIELD

The present invention generally relates to a medical surgical device and specifically a wire guide for percutaneous placement within a body cavity.

BACKGROUND

Wire guides are commonly used in vascular procedures, such as angioplasty procedures, diagnostic and interventional procedures, percutaneous access procedures, or radiological and neuroradiological procedures in general, to introduce a wide variety of medical devices into the vascular system. For example, wire guides are used for advancing intraluminal devices such as stent delivery catheters, balloon dilation catheters, atherectomy catheters, and the like within body lumens. Typically, the wire guide is positioned inside the inner lumen of an introducer catheter. The wire guide is advanced out of the distal end of the introducer catheter into the patient until the distal end of the wire guide reaches the location where the interventional procedure is to be performed. After the wire guide is inserted, another device such as a stent and stent delivery catheter is advanced over the previously introduced wire guide into the patient until the stent delivery catheter is in the desired location. After the stent has been delivered, the stent delivery catheter can then be removed from a patient by retracting the stent delivery catheter back over the wire guide. The wire guide may be left in place after the procedure is completed to ensure easy access if it is required.

Conventional wire guides include an elongated wire core with one or more tapered sections near the distal end to increase flexibility. Generally, a flexible body such as a helical coil or tubular body is disposed about the wire core. The wire core is secured to the flexible body at the distal end. In addition, a torquing means can be provided on the proximal end of the core member to rotate, and thereby steer a wire guide having a curved tip, as it is being advanced through a patient's vascular system.

A major requirement for wire guides and other intraluminal guiding members, is that they have sufficient stiffness to be pushed through the patient's vascular system or other body lumen without kinking. However, they must also be flexible enough to pass through the tortuous passageways without damaging the blood vessel or any other body lumen through which they are advanced. Efforts have been made to improve both the strength and the flexibility of wire guides to make them more suitable for their intended uses, but these two properties tend to be diametrically opposed to one another in that an increase in one usually involves a decrease in the other.

For certain procedures, such as when delivering stents around challenging take-off, tortuosities, or severe angulation, substantially more support and/or vessel straightening is frequently needed from the wire guide. Wire guides have been commercially available for such procedures which provide improved support over conventional wire guides. However, such wire guides are in some instances are so stiff they can damage vessel linings when being advanced.

In other instances, extreme flexibility is required as well. For example, when branched or looped stents are to be delivered to a branched vascular region, it is beneficial to insert the wire guide from the branch where a stent is to be located. However, the stent may need to be introduced and guided from a separate branch. In this situation, the wire guide is inserted into the patient's vascular system near the desired stent location and a grasping device is inserted in the branch from which the stent will be introduced. The wire guide may be advanced back along the branch to provide the grasping device access to the distal end of the wire guide. However, the wire guide should be extremely flexible to allow grasping and manipulation of the wire guide without damaging the tissue around the bifurcation formed by the luminal branch. Further, the wire guide should be extremely kink resistant to avoid damaging the wire guide as it is grasped. After the wire guide is retrieved by the grasping device, the stent may be delivered over the wire guide to the desired location. However, available wire guides are not designed to provide the flexibility required to cross up and over the bifurcation of the luminal branch and yet also provide the stiffness required to aid in the insertion of the stent. In view of the above, it is apparent that there exists a need for an improved design for a wire guide.

BRIEF SUMMARY

One aspect provides a wire guide including an elongated core member having a proximal stop, a distal stop and a rib positioned between the proximal stop and the distal stop. A first coil is positioned over the elongated core member and extends between the proximal stop and the rib. A second coil is positioned over the elongated core member and extends between the rib and the distal stop. In one embodiment, the first coil and the second coil are attached to the rib. The coils may be attached to the rib by welding. The rib may be an enlarged cross-sectional portion of the elongated core element.

In another embodiment, the distal stop is formed by a distal tip attached to the distal end of the elongated core member. In yet another embodiment, at least one of the first coil and the second coil is formed from a wire. In another embodiment, the rib extends axially along the elongated core member for a distance of less than twice the cross-sectional dimension of the wire. In one embodiment, the cross-sectional dimension is between $1/50$ inch and $1/500$ inch. In another embodiment, the cross-sectional dimension is between $1/100$ inch and $1/200$ inch.

In one embodiment, wherein the elongated core member includes stainless steel, a stainless steel alloy, a nickel-titanium alloy or combinations thereof. In another embodiment, the region of the elongated core member between the rib and the distal stop includes at least one taper reducing a cross-section of a distal portion of that region relative to a proximal portion of that region.

In another embodiment, at least one of the first coil and the second coil includes stainless steel or a stainless steel alloy. In yet another embodiment, the outside dimension and the first coil is greater than the outside dimension of the second coil.

In one embodiment, the elongated core element, the first coil, the second coil or the distal tip includes a radiopaque material. In another embodiment, the wire guide also includes a coating on at least of the first coil and the second coil. The coating may include a polymer.

DETAILED DESCRIPTION

In accordance with one embodiment, a wire guide system includes a wire guide for use in medical procedures. As used herein, the term "proximal" refers to that portion of the wire guide closest to a physician when placing the wire guide in the patient, and the term "distal" refers to that portion of the wire guide closest to the end inserted into the patient's body.

Figure 1:
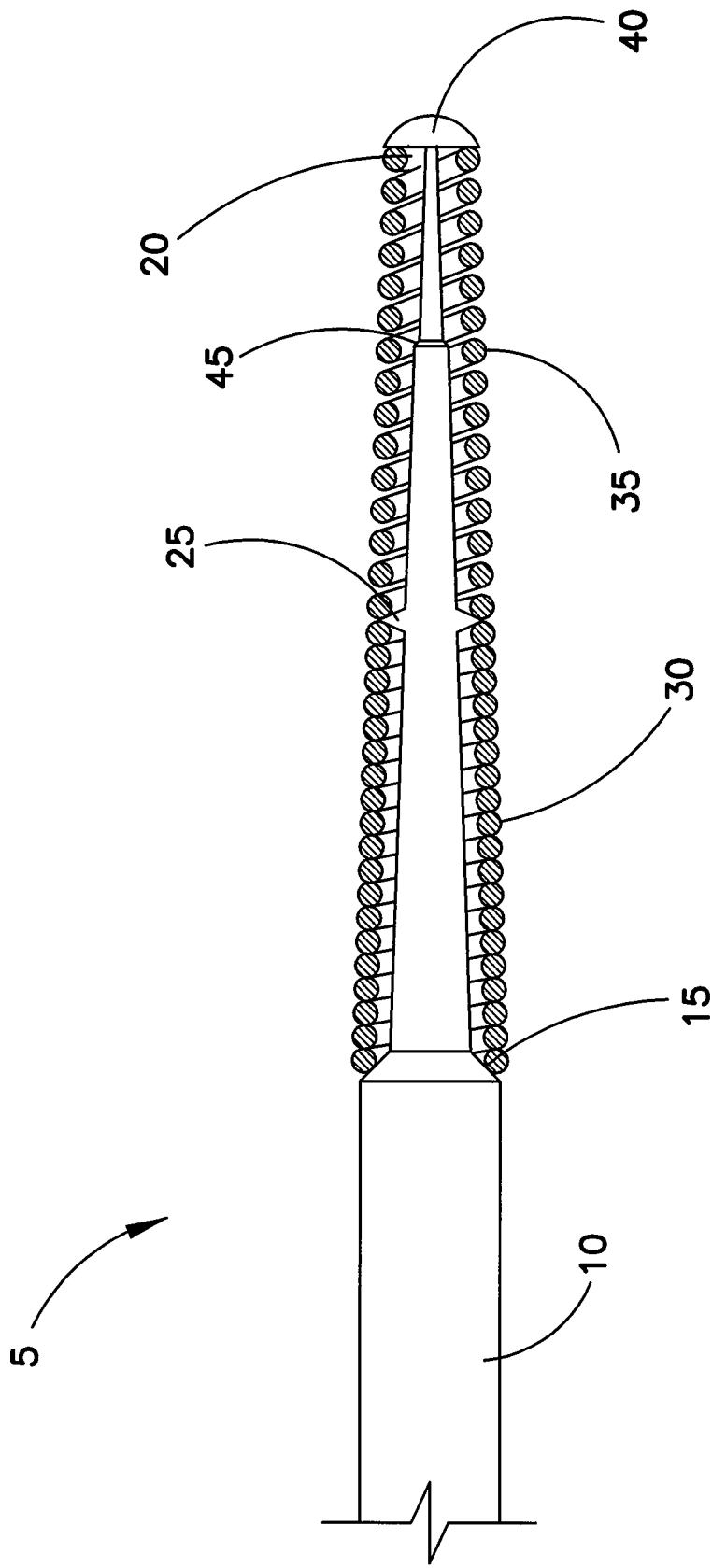
FIG. 1 shows one embodiment of an illustrative wire guide.

Referring now to FIG. 1, this figure illustrates one embodiment of a wire guide 5 including elongated core member 10 having proximal stop 15 and a distal stop 20. Rib 25 is positioned on elongated core member 10 between the proximal stop 15 and the distal stop 20. First coil 30 is positioned over elongated core member 10 and extends between proximal stop 15 and rib 25. Second coil 35 is positioned over elongated core member 10 and extends between rib 25 and distal stop 20. At least one of first coil 30 and second coil 35 is attached to rib 25. In one embodiment, distal stop 20 in formed by distal tip 40 attached to the distal end of elongated core member 10.

In one embodiment, elongated core member 10 includes at least one taper 45 reducing the cross-section of elongated core member 10 between rib 25 and distal stop 20. Of course, more than one taper may be present. The portion of elongated core member 10 between proximal stop 15 and rib 25 may also include one or more tapers. A taper may also be placed at rib 25 so that the portion of elongated core member 10 distal of rib 25 has a different cross-section than that portion of elongated core member 10 between rib 25 and proximal stop 15.

The presence of tapers in elongated core member 10 allows the flexibility of elongated core member 10 to be varied along its length. In one embodiment, tapers are introduced so that elongated core member 10 is less flexible towards the distal end.

Figure 2:
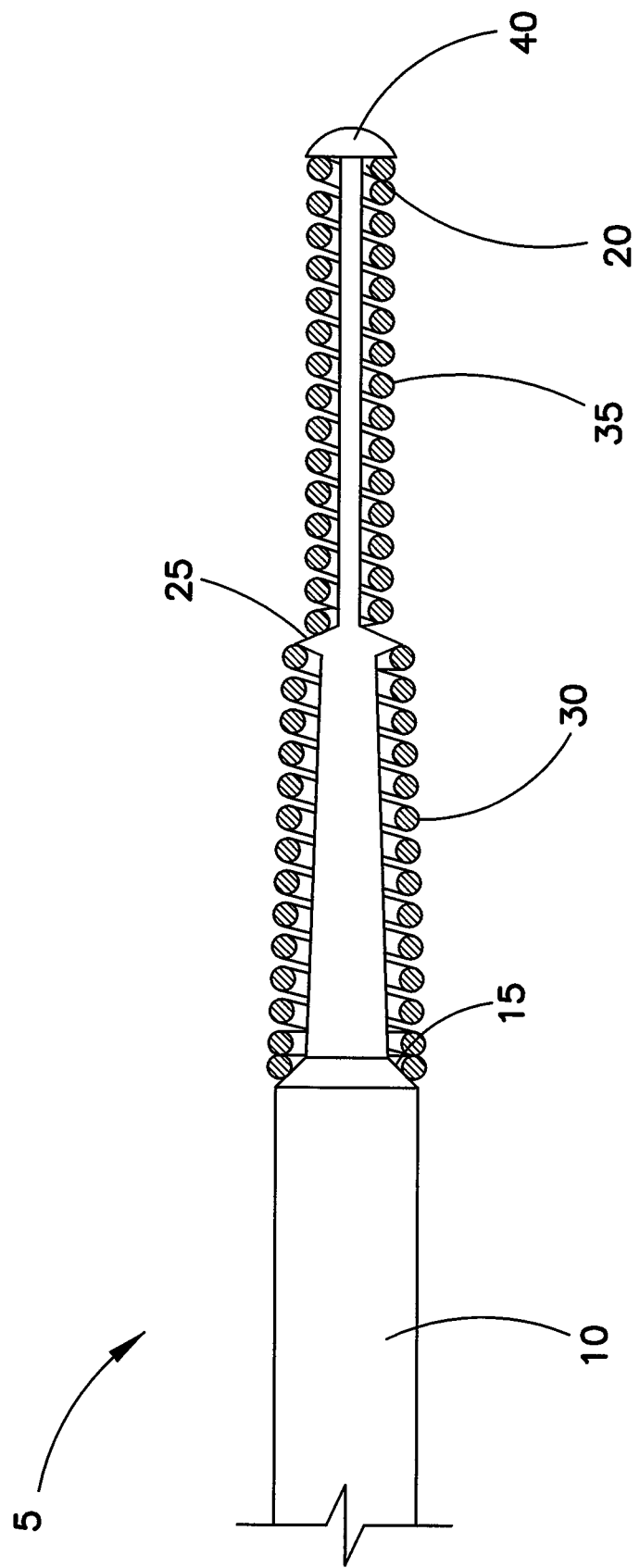
FIG. 2 shows another embodiment of an illustrative wire guide.

First coil 30 and second coil 35 may be formed from the same or form different materials. In one embodiment, these coils are formed from wire having a substantially constant cross-section. In such embodiments, the cross-section of the wire forming first coil 30 may be the same, or be different from, the cross-section of the wire forming second coil 35. In one embodiment, illustrated in FIG. 2, the outside dimension of first coil 30 is greater that the outside dimension of second coil 35. In one embodiment, the cross-sectional dimension of the wire forming first coil 30 is between 1/50 inch and 1/500 inch. In another embodiment, the cross-sectional dimension of the wire forming first coil 30 is between 1/100 inch and 1/200 inch.

Figure 3:
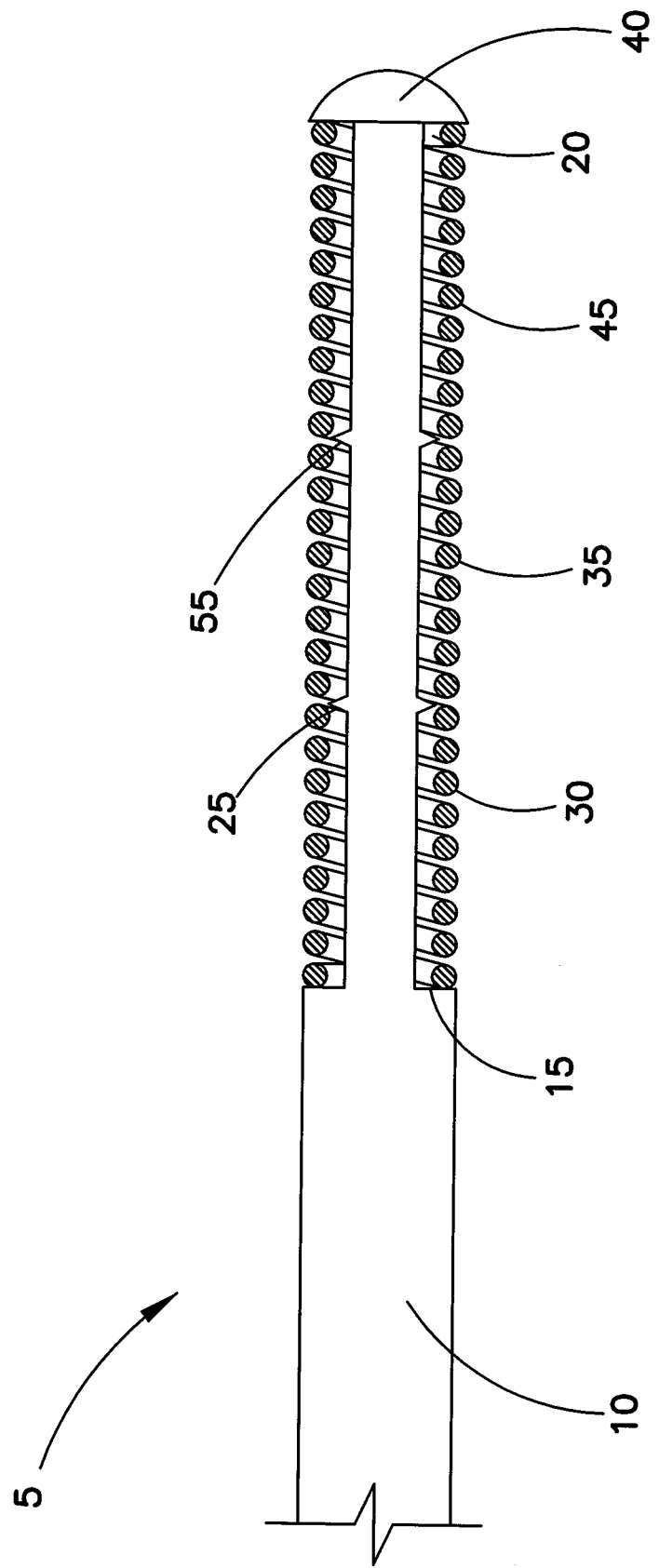
FIG. 3 shows yet another embodiment of an illustrative wire guide.

FIG. 3 illustrates yet another embodiment of a wire guide. Wire guide 5 again includes elongated core member 10 having proximal stop 15 and distal stop 20. In this embodiment, proximal rib 25 is positioned on elongated core member 10 between the proximal stop 15 and distal stop 20. First coil 30 is positioned over elongated core member 10 and extends between proximal stop 15 and proximal rib 25. Second coil 35 is positioned over elongated core member 10 and extends between proximal rib 25 and distal rib 55. In addition, third coil 45 is positioned over elongated core member 10 and extends between distal rib 55 and distal stop 20. Of course, the present embodiments contemplate a wire guide having three, four or more ribs and associated coils.

The materials used to form the coils and the cross-section of wire forming the coils may be chosen to control the flexibility of the coils, and hence the flexibility of wire guide 5. The pitch of the coils and the outside dimension of these coils may also be varied so control the flexibility of the coils. The presence of the rib allows the flexibility of portions of wire guide 5 distal and proximal of the ribs to be varied independently by varying the flexibility of the coils.

In various embodiments, the axial distance from proximal stop 15 to the center of rib 25 is between 5% and 10%, 10% and 20%, 20% and 30%, 30% and 40%. 40% and 50%, 50% and 60%, 60% and 70%, 70% and 80%, or 80% and 90% of the axial distance between proximal stop 15 and distal stop 20.

In one embodiment, the thickness of the ribs, i.e. the distance the ribs extends along elongated core member 10, is chosen to reduce or eliminate the impact the presence of the ribs has on the flexibility of wire guide 5. In one embodiment, the thickness of at least one of the ribs is less than twice the minimum cross-sectional dimension of the wire forming the coils. In another embodiment, the thickness of at least one of the ribs is less than the minimum cross-sectional dimension of the wires forming the coils.

The wire guide 5 may have typical wire guide dimensions. The wire guide length may generally be about 90 to about 300 cm, and for use within a patient's coronary system available wire guides are typically about 180 cm in length.

In certain embodiments, elongated core element 10 is manufactured from a material such as stainless steel, a stainless steel alloy, a nickel-titanium alloy, such as nitinol, or combinations of these materials. The coils may also be formed of such materials. The coils may be formed of the same or of different materials. In certain embodiments, elongated core element 10 includes a radiopaque material, such as platinum or gold, which allows for better visibility during manipulation of the wire guide 5 within the body of the patient. In certain other embodiments, a radiopaque material is included in other portions of wire guide 5, for example, as part of distal tip 40 and/or the first coils.

In certain embodiments, wire guide 5 further includes a coating on at least a portion of the outer surface of at least one of the coils. The coating can include a material that reduces the coefficient of friction on that surface. For example, the coating may include a polymer such as, but not limited to, a fluoropolymer.

The rib(s) may be a raised (enlarged cross-sectional portion) of the elongated core element 10. In one embodiment, the ribs are formed by grinding a portion of core element 10. For example, a rib may be formed by grinding a core element, formed from stainless steel, a stainless steel alloy or nickel-titanium alloy, using a CAM.2 profile grinder (Glebar Company, Inc., Franklin Lakes, N.J., 07417). Using the technique, a length tolerance of better that 0.001" and a diameter tolerance of better than 0.0001" may be obtained.

The coils can be attached to elongated core element 10 by methods including, but not limited to, adhesive, solder or welding, including laser welding. In one embodiment, the inside surface of at least one of the coils is welded to at least one rib by a spot joint formed by a laser.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A wire guide comprising:
   a distal tip,
   an elongated core member extending from a proximal stop to a distal end and comprising a raised portion between the proximal stop and the distal end, wherein the distal end attaches to the distal tip,
   a first coil positioned over the elongated core member and extending from the proximal stop to the raised portion, and
   a second coil positioned over the elongated core member and extending from the raised portion to the distal end,
   wherein the first coil and the second coil attach to the raised portion and wherein the raised portion is formed by grinding a portion of the elongated core element.

2. The wire guide of claim 1, wherein at least one of the first coil and the second coil attach to the raised portion by a welded joint.

3. The wire guide of claim 2, wherein at least one of the first coil and the second coil attach to the raised portion by a welded spot joint formed by a laser.

4. The wire guide of claim 1, wherein at least one of the first coil and the second coil is formed from a wire having a cross-sectional dimension and wherein the raised portion extends axially along the elongated core member for a distance of less than twice the cross-sectional dimension.

5. The wire guide of claim 4, wherein the cross-sectional dimension is between 1/50 inch and 1/500 inch.

6. The wire guide of claim 5, wherein the cross-sectional dimension is between 1/100 inch and 1/200 inch.

7. The wire guide of claim 1, wherein the elongated core member comprises at least one material selected from the group consisting of stainless steel, nickel and titanium.

8. The wire guide of claim 1, wherein the elongated core member comprises at least one taper between the raised portion and the distal stop.

9. The wire guide of claim 1, wherein at least one of the first coil and the second coil comprises stainless steel.

10. The wire guide of claim 1, wherein the first coil has a first outside dimension and the second coil has a second outside dimension and wherein the first outside dimension is greater than the second outside dimension.

11. The wire guide of claim 1, wherein the at least one of the elongated core element, the first coil, the second coil, and the distal tip comprises a radiopaque material.

12. The wire guide of claim 1, further comprising a coating on at least one of the first coil and the second coil.

13. The wire guide of claim 12, wherein the coating comprises a polymer.

14. The wire guide of claim 12, wherein the coating reduces the coefficient of friction of a surface of at least one of the first coil and the second coil.

15. The wire guide of claim 13, wherein the polymer is a fluoropolymer.

* * * * *